United States Patent [19]

Glavan et al.

[11] 4,374,821
[45] Feb. 22, 1983

[54] MYOCARDIAL IMAGING AGENT AND METHOD

[75] Inventors: Kenneth A. Glavan; James F. Kronauge, both of Plainsboro, N.J.

[73] Assignee: E. R. Squibb & Sons, Inc., Princeton, N.J.

[21] Appl. No.: 392,811

[22] Filed: Jun. 28, 1982

[51] Int. Cl.³ .................. A61K 49/04; C07F 9/28; C07F 13/00
[52] U.S. Cl. .................................. 424/4; 260/429 R
[58] Field of Search ........................ 424/4; 260/429 R

[56] References Cited

U.S. PATENT DOCUMENTS 3,695,853  10/1972  Klanberg ................. 260/429 R
3,987,157  10/1976  Molinski et al. ........... 260/429 R
4,017,596   4/1977  Loberg et al. ............. 260/429 R

FOREIGN PATENT DOCUMENTS 38756    4/1981  European Pat. Off.
1152414  8/1963  Fed. Rep. of Germany ... 260/429 R

OTHER PUBLICATIONS

J. Nucl. Med., 21 (6): p. P56, (1980).
J. Nucl. Med., 22 (6): p. P51, (1981).
Nature, 1959, pp. 1039–1040.
J. Chem. Soc., (London), 1950, pp. 851–856.
Deutsch, Glavan et al., "Cationic Tc-99m Complexes as Potential Myocardial Imaging Agents", J. Nucl. Med. 22:897–907, 1981.
Deutsch et al., "Heart Imaging with Cationic Complexes of Technetium", Science, 214, Oct. 2, 1981, 85–86.

Primary Examiner—Joseph E. Evans
Attorney, Agent, or Firm—Lawrence S. Levinson; Burton Rodney

[57] ABSTRACT

A myocardial imaging agent is provided having the structure

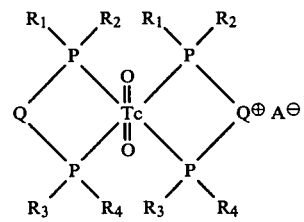

wherein Q, $R_1$, $R_2$, $R_3$ and $R_4$ and A are as defined herein. A method for scanning the heart, liver or kidneys employing the above agent is also provided.

16 Claims, No Drawings

MYOCARDIAL IMAGING AGENT AND METHOD

BACKGROUND OF THE INVENTION

European Patent Application No. 0 038 756 to Deutsch and Glavan discloses cationic lipophilic complexes of technetium-99m that are useful as negative heart imaging agents in that they accumulate in the normal heart and visualize an infarct as a cold area on a relatively hot background of normal tissue.

The subject complexes of technetium-99m have lipophilic ligands and an overall cationic charge and are described by the formula $$[(L)_2{}^{99m}Tc(X)_2]^{\oplus}X^{\ominus},$$

wherein each L represents the same or different lipophilic ligand strongly chelating for a technetium-99m cation, and wherein the three X's are the same or different monovalent anionic ligand. Examples of such complexes include 99m-Tc(diars)$_2$X$_2^+$ wherein diars is o-C$_6$H$_4$(As(CH$_3$)$_2$)$_2$ (o-phenylenebis (dimethylarsine)) and X$_2$ is Cl or Br, trans-99m-Tc(dmpe)$_2$Cl$_2^+$ (wherein dmpe is (CH$_3$)$_2$P-CH$_2$CH$_2$-P(CH$_3$)$_2$) which is said to be the preferred myocardial imaging agent and 99m-Tc(tetraphos)Cl$_2^+$ (wherein tetraphos is P(CH$_2$CH$_2$P(C$_6$H$_5$)$_2$)$_3$).

The above-described complexes are prepared by Deutsch and Glavan using the following procedure. The ligand and technetium-99m (in the form of pertechnetate ion or reduced derivative thereof) are first complexed in a mono- or biphasic system employing a large (preferably greater than ten fold) excess of lipophilic ligand over technetium. The resulting complex is isolated and purified using standard chromatographic techniques. Finally, the "purified" complex is dissolved (or suspended) in a pharmacologically acceptable administration vehicle. Among the vehicles suggested by Deutsch and Glavan are saline, 50/50 ethanol/saline, vehicles wherein the concentration of ethanol is varied, vehicles wherein ethanol is replaced by other organic portions such as propylene glycol, glycerol or dimethyl sulfoxide, or vehicles based on solubilization of the radiopharmaceutical in micelles.

DESCRIPTION OF THE INVENTION

The compounds of the present invention are useful for measuring myocardial perfusion and the diagnosis of ischemia and infarction as well as an imaging agent for the liver and kidneys and have the general formula.

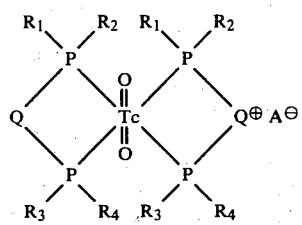

wherein Q is a $-(CH_2)_n-$ linking group wherein n is 2 to 8, and preferably 2 to 5, or Q is a 1,2-phenylene group

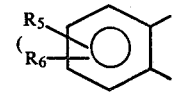

wherein R$_5$ and R$_6$ are independently selected from hydrogen, lower alkyl, or halogen) and R$_1$, R$_2$, R$_3$ and R$_4$ are independently the same or different and are hydrogen, lower alkyl, or phenyl, and A represents an anion group as defined hereinafter.

Thus, the compounds of the invention may have the formula:

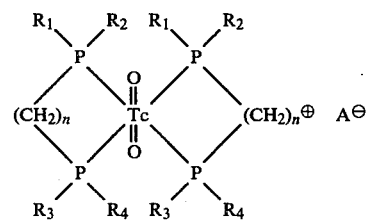

or

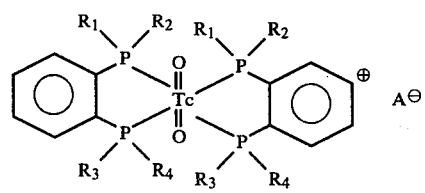

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halosubstituent, such as F, Br, Cl or I or CF$_3$, an alkoxy substituent, an aryl substituent, an alkyl-aryl substituent or a haloaryl substituent.

The term "halogen" or "halo" as used herein refers to chlorine, bromine, fluorine or iodine with Cl or Br being preferred.

The term "(CH$_2$)$_n$" includes a straight or branched chain radical having from 2 to 8 carbons in the normal chain and preferably from 2 to 5 carbons in the normal chain and may contain one or more lower alkyl substituents. Examples of (CH$_2$)$_n$ groups include CH$_2$CH$_2$, (CH$_2$)$_3$, (CH$_2$)$_4$, (CH$_2$)$_5$, (CH$_2$)$_6$, (CH$_2$)$_7$,

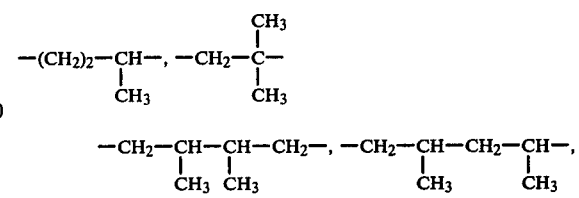

and the like.

Preferred are those compounds of formula I wherein Q is (CH$_2$)$_2$, and R$_1$, R$_2$, R$_3$ and R$_4$ are each methyl, ethyl, n-propyl, n-butyl or phenyl, or Q is

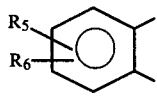

and $R_5$ and $R_6$ are each hydrogen, and $R_1$, $R_2$, $R_3$ and $R_4$ are each methyl or any of the other alkyl groups listed above or phenyl.

The various compounds of the invention may be prepared as outlined below.

The compounds of formula I may be prepared by reacting ammonium pertechnetate (VII) ($NH_4TcO_4$) with excess ligand of the structure

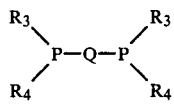   IV at reflux temperature, preferably in the presence of a source of anion ($A^{\ominus}$) and an inert organic solvent, such as acetone, methylene chloride, methanol or ethanol. The reaction will be run at a temperature of from about 30° to about 180° C., and preferably from about 30° to about 130° C.

In carrying out the above reaction, the ligand IV is employed in a molar ratio to the ammonium pertechnetate of within the range of from about 2.5:1 to about 10:1, preferably from about 3:1 to about 5:1, and optimally about 4:1.

The concentration of anion is not critical, but it does govern the rate of the ligand exchange reaction; preferably the anion will be present in an amount sufficient to provide a concentration of 0.5 molar after the technetium-99m has been added.

The formulation can also contain various adjuvants including preservatives, such as alkyl parabens (e.g., methyl paraben and propyl paraben), and solubilizing agents for the ligand (e.g., PVP, ethylene glycol distearate, glycol and phenyl salicylic acid.

Examples of ligands which may be employed in forming the compounds of the invention include the following:

bis(1,2-dimethylphosphino)ethane, also known as "dmpe", that is

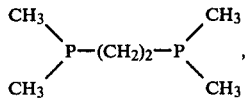

bis(1,2-diphenylphosphino)ethane, also known as "diphos", that is

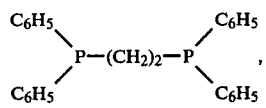

1,2-bis(dihydrophosphino)ethane, that is

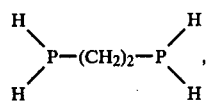

bis(1,2-diethylphosphino)ethane, also known as "depe", that is

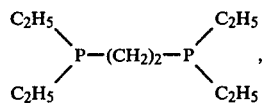

bis(1,2-di-n-propylphosphino)ethane, also known as "dppe", that is

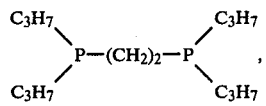

bis(1,2-di-n-butylphosphino)ethane, also known as "dbpe", that is

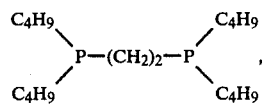

o-phenylene bis(dimethylphosphine), that is

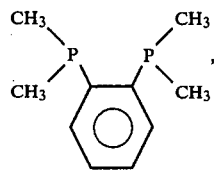

o-phenylene bis(dihydrophosphine), that is

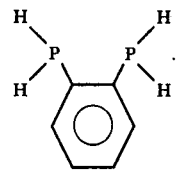

The above ligands are exemplary. It will be appreciated that any ligand falling within the scope of formula IV may be employed. The preferred ligands are dmpe, diphos and o-phenylene bis(dimethylphosphine).

As indicated, anion ($A^{\ominus}$) is present when the ammonium pertechnetate (VII) is added to the ligand. The anion (in the form of a salt) will preferably comprise a halogen, such as $Cl^-$, $Br^-$, $F^-$ or $I^-$, $ClO_4^-$, $PF_6^-$, $BF_4^-$, $SCN^-$ or any other pharmaceutically acceptable anion with $Cl^-$ being preferred.

Technetium-99m is available as a product from commercial sources such as manufacturing companies and radiopharmacies. Because of the relatively short half-life of technetium-99m it is most desirable to generate the radionuclide as close to its time of use as possible. The most common source of technetium-99m is the parent-daughter generator. Molybdenum-99 (the "parent" radionuclide) is maintained on a containerized support medium (usually alumina) and, when eluted with the proper eluant (usually saline) technetium-99m in the form of pertechnetate ion ($^{99m}TcO_4^{\ominus}$) is generated; see, for example, U.S. Pat. Nos. 3,369,121 and 3,920,995.

The following Examples represent preferred embodiments of the invention. All temperatures are expressed in °C.

EXAMPLE 1

Dioxobis[(1,2-dimethylphosphino)ethane]technetium (V) Perchlorate

Ammonium pertechnetate (VII), that is $NH_4TcO_4$ (0.2343 g, 1.3 mmoles), lithium perchlorate (0.18324 g, 1.7 mmoles), methylene chloride (100 ml) and acetone (50 ml) were placed into a two-necked 250 ml round bottom flask equipped with water-cooled condenser, inlet-outlet tubes, and Teflon ®-coated stir bar. The apparatus was flushed with nitrogen and then bis(1,2-dimethylphosphino)ethane ligand (0.77 g, 5.2 mmoles) was added to the flask. The reaction was stirred and heated under reflux for 2.5 hours. The resulting orange-yellow solution was allowed to cool to room temperature depositing a reddish precipitate. The solution and the precipitate were concentrated, under vacuum, to dryness. The residue was dissolved in the minimal quantity of methylene chloride and then toluene was added to the dichloromethane solution resulting in the deposition of a tan precipitate. The precipitate was removed by filtration, washed with toluene to remove excess bis(1,2-dimethylphosphine)ethane and with anhydrous ethyl ether to remove excess lithium chlorate, and air dried to yield 0.685 g (99.8%) of the title product.

EXAMPLE 2

Dioxobis[(1,2-diethylphosphino)ethane]technetium (V) Perchlorate

Ammonium pertechnetate (VII), that is $NH_4TcO_4$ (0.12575 g, 0.69 mmoles), lithium perchlorate (0.14405 g, 1.4 mmoles), methylene chloride (100 ml) and acetone (50 ml) were placed into a three-necked 250 ml round bottom flask equipped with water-cooled condenser, inlet-outlet tubes, and Teflon ®-coated stir bar. The apparatus was flushed with nitrogen and then bis(1,2-diethylphosphino)ethane ligand (0.57 g, 2.8 mmoles) was added by syringe to the flask. The reaction was stirred and heated under reflux for 9 hours. The resulting golden-yellow solution was concentrated, under vacuum, to dryness. The brown residue was dissolved in a toluene-methylene chloride mixture and then anhydrous ethyl ether was added to precipitate a brown product. The precipitate was removed by filtration, washed with toluene and with anhydrous ethyl ether and dried in vacuo to yield 0.38821 (86.9%) of the title product.

EXAMPLE 3

[Dioxobis[(1,2-di-n-propylphosphino)ethane]technetium (V) Perchlorate

Ammonium pertechnetate (VII), that is $NH_4TcO_4$ (0.13008 g, 0.72 mmoles), lithium perchlorate (0.13758 g, 1.3 mmoles), methylene chloride (100 ml) and acetone (50 ml) were placed into a three-necked 250 ml round bottom flask equipped with water-cooled condenser, inlet-outlet tubes, and Teflon ®-coated stir bar. The apparatus was flushed with nitrogen for 10 minutes and then bis(1,2-di-n-propylphosphino)ethane ligand (0.87 g, 3.3 mmoles) was added to the flask. The reaction was stirred and heated under reflux for 1.5 hours. The resulting golden-yellow solution was concentrated, under vacuum, to dryness. The brown residue was washed with toluene to remove excess bis(1,2n-propylphosphine)ethane and with anhydrous ethyl ether to remove excess lithium chlorate, and dried in vacuo, to yield 0.30880 (56.9%) of the title product.

EXAMPLE 4

[Dioxobis[(1,2-di-n-butylphosphino)ethane]technetium (V) Perchlorate

Ammonium pertechnetate (VII), that is $NH_4TcO_4$ (0.14064 g, 0.78 mmoles), lithium perchlorate (0.14551 g, 1.4 mmoles), methylene chloride (100 ml) and acetone (50 ml) were placed into a three-necked 250 ml round bottom flask equipped with water-cooled condenser, inlet-outlet tubes, and Teflon ®-coated stir bar. The apparatus was flushed with nitrogen and then bis(1,2di-n-butylphosphino)ethane ligand (1.10 g, 3.5 mmoles) was added to the flask. The reaction was stirred and heated under reflux for 2.5 hours. The resulting golden-yellow solution was concentrated under vacuum, to dryness. The orange-brown residue was dissolved in methylene chloride, filtered to remove excess lithium chlorate and loaded onto a 2 cm ID×10 cm Fisher alumina acid (Brockman Activity I) column prepared with methylene chloride. Upon loading, an orange-brown band remained adsorbed to the column resin. The column was washed with methylene chloride to remove excess bis(1,2-di-n-butylphosphine)ethane and the band was subsequently eluted with anhydrous methanol; the methanol was allowed to evaporate to dryness and the residue was dissolved in petroleum ether (orange solution), and hexafluorophosphate ($LiPF_6$) was added to obtain a tan precipitate.

EXAMPLE 5

Dioxobis[(1,2-diphenylphosphino)ethane]technetium (V) Perchlorate

Ammonium pertechnetate (VII), that is $NH_4TcO_4$ (0.12768 g, 0.7 mmoles), lithium perchlorate (0.122 g, 1.15 mmoles), bis(1,2-diphenylphosphino)ethane (1.5 g, 2.89 mmoles) and acetone (250 ml) were placed into a three-necked 500 ml round bottom flask equipped with water-cooled condenser, inlet-outlet tubes, and Teflon ®-coated stir bar. The apparatus was flushed with nitrogen for 10 minutes and then was stirred and heated under reflux for 21 hours. The resulting solution was concentrated, under vacuum, to dryness. The residue was washed with methylene chloride and with anhydrous ethyl ether to yield 410 mg (56.6%) of the title product in the form of a tan solid.

EXAMPLE 6

Dioxobis[(1,2-dimethylphosphino)benzene]technetium (V) Perchlorate

Ammonium pertechnetate (VII), that is $NH_4TcO_4$ (0.11341 g, 0.63 mmoles), lithium perchlorate (0.1000 g, 0.94 mmoles), and acetate (150 ml) were placed into a three-necked 250 ml round bottom flask equipped with water-cooled condenser, inlet-outlet tubes, and Teflon ®-coated stir bar. The apparatus was flushed with nitrogen for 20 minutes and then bis(1,2-dimethylphosphine)benzene (i.e., o-phenylene-bis(dimethylphosphino)) ligand (0.8 g, 4.0 mmoles) was added to the flask. The reaction was stirred and heated under reflux for 4 hours. The resulting golden-yellow solution was concentrated, under vacuum, to dryness. The yellow-brown residue was washed with methylene chloride to remove excess bis(1,2-dimethylphosphine)benzene and with anhydrous ethyl ether to remove excess lithium perchlorate and dried, in vacuo, to yield 0.4320 g (95%) of the title product.

EXAMPLE 7

Dioxobis[(1,2-dimethylphosphino)ethane]technetium (V) chloride

Sodium pertechnetate (VII) (0.25 ml) from a Minitec Generator, distilled water (0.9 ml), 95% ethanol (0.1 ml), and bis(1,2-dimethylphosphino)ethane ligand (0.20 ml) were placed into a stoppered 5 ml serum vial. The vial was vigorously shaken for 5 minutes, and then 2 ml of methylene chloride containing 0.1 g of tetrabutyl-ammonium chloride were added to the vial. The vial was again vigorously shaken for 5 minutes. The aqueous phase containing the cationic technetium complex was subsequently removed.

EXAMPLE 8

Dioxobis[(1,2-diethylphosphino)ethane]technetium (V) chloride

Sodium pertechnetate (VII) (0.25 ml) from a Minitec Generator, distilled water (0.9 ml), 95% ethanol (0.1 ml), and bis(1,2-diethylphosphino)ethane ligand (0.20 ml) were placed into a stoppered 5 ml serum vial. The vial was heated for 60 minutes at 40° C. and then cooled to room temperature. Methylene chloride (2 ml) containing 0.1 g of tetrabutyl-ammonium chloride was added to the vial. The vial was vigorously shaken for 5 minutes. The aqueous phase containing the cationic technetium complex was subsequently removed.

What is claimed is:

1. A technetium complex having the structure

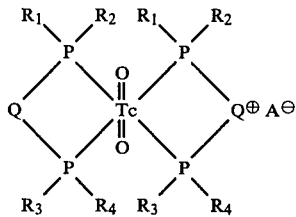

wherein Q is a —(CH$_2$)$_n$—linking group wherein n is 2 to 8, or a 1,2-phenylene linking group,
R$_1$, R$_2$, R$_3$ and R$_4$ are independently the same or different and are hydrogen, lower alkyl or phenyl, and
A represents an anion group.

2. The complex as defined in claim 1 wherein Q is —(CH$_2$)$_n$—.

3. The complex as defined in claim 1 wherein Q is

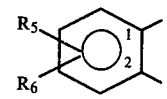

wherein R$_5$ and R$_6$ are independently selected from hydrogen, lower alkyl or halogen.

4. The complex as defined in claim 1 wherein R$_1$, R$_2$, R$_3$ and R$_4$ are each lower alkyl.

5. The complex as defined in claim 1 wherein R$_1$, R$_2$, R$_3$ and R$_4$ are each phenyl.

6. The complex as defined in claim 1 having the name dioxobis[(1,2-dimethylphosphino)ethane]technetium perchlorate.

7. The complex as defined in claim 1 having the name dioxobis](1,2-diethylphosphino)ethane]technetium perchlorate.

8. The complex as defined in claim 1 having the name dioxobis[(1,2-dimethylphosphino)ethane]technetium (V) chloride.

9. The complex as defined in claim 1 having the name dioxobis[(1,2-diethylphosphosphino)ethane]technetium (V) chloride.

10. The complex as defined in claim 1 having the name dioxobis[(1,2-di-n-propylphosphino)ethane]technetium perchlorate.

11. The complex as defined in claim 1 having the name dioxobis[(1,2di-n-butylphosphino)ethane[technetium perchlorate.

12. The complex as defined in claim 1 having the name dioxobis[(1,2-diphenylphosphino)ethane]technetium perchlorate.

13. The complex as defined in claim 1 having the name dioxobis[(1,2-dimethylphosphino)benzene]technetium perchlorate.

14. An imaging composition for the heart, liver or kidneys, comprising a complex as defined in claim 1 and a pharmaceutically acceptable carrier therefor.

15. A method for scanning the heart which comprises injecting intravenously the complex as defined in claim 1 in a pharmaceutically acceptable vehicle and scanning the heart.

16. A method for scanning the liver or kidneys which comprises injecting intravenously the complex as defined in claim 1 in a pharmaceutically acceptable vehicle and scanning the liver or kidneys.

* * * * *

UNITED STATES PATENT AND TRADEMARK OFFICE
CERTIFICATE OF CORRECTION

PATENT NO. : 4,374,821

DATED : February 22, 1983

INVENTOR(S) : Kenneth A. Glavan et al.

It is certified that error appears in the above—identified patent and that said Letters Patent is hereby corrected as shown below:

Column 1, next to the structure on line 60, insert --I--.
Column 3, structure IV should read

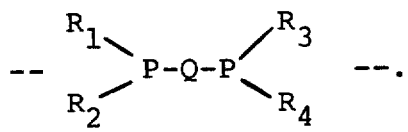

Column 6, line 6, delete the bracket before "Dioxobis".

Signed and Sealed this

Seventeenth Day of May 1983

[SEAL]

Attest:

DONALD J. QUIGG

Attesting Officer    Acting Commissioner of Patents and Trademarks